United States Patent [19]
Drent

[11] Patent Number: 5,028,734
[45] Date of Patent: Jul. 2, 1991

[54] PROCESS FOR THE SELECTIVE PREPARATION OF ALKENECARBOXYLIC ACID DERIVATIVES

[75] Inventor: Eit Drent, Amsterdam, Netherlands

[73] Assignee: Shell Oil Company, Houston, Tex.

[21] Appl. No.: 303,596

[22] Filed: Jan. 27, 1989

Related U.S. Application Data

[62] Division of Ser. No. 127,330, Dec. 2, 1987, abandoned.

[30] Foreign Application Priority Data

Dec. 10, 1986 [NL] Netherlands ..................... 8603139

[51] Int. Cl.$^5$ ...................... C07C 67/38; C07C 51/14
[52] U.S. Cl. ..................................... 560/207; 560/97; 560/114; 560/204; 560/233; 562/406; 562/477; 562/522; 562/890; 260/410.9 R; 260/410.6; 260/413; 536/119
[58] Field of Search ............... 560/233, 207, 97, 114, 560/204; 562/406, 497, 522, 890; 536/119; 260/410.9 R, 410.6, 413, 546

[56] References Cited

U.S. PATENT DOCUMENTS

| | | | |
|---|---|---|---|
| 3,501,518 | 3/1970 | von Kutepow | 562/522 |
| 3,530,155 | 9/1970 | Fenton | 562/522 |
| 4,124,617 | 11/1978 | Knifton | 562/522 |
| 4,172,087 | 10/1979 | Knifton | 562/522 |
| 4,243,829 | 1/1981 | Pittman | 585/511 |
| 4,414,409 | 11/1983 | Waller | 562/522 |
| 4,582,817 | 4/1986 | Hanes | 502/162 |

FOREIGN PATENT DOCUMENTS

| | | |
|---|---|---|
| 190473 | 8/1986 | European Pat. Off. . |
| 198521 | 10/1986 | European Pat. Off. . |
| 1110405 | 4/1968 | United Kingdom . |
| 2058074 | 4/1981 | United Kingdom . |

Primary Examiner—José G. Dees
Attorney, Agent, or Firm—Y. Grace Tsang

[57] ABSTRACT

A process for the selective carbonylation of a conjugated diene by contacting with carbon monoxide in the presence of a hydroxyl-group-containing compound such as water, alcohol, phenol or carboxylic acid in liquid phase using a catalyst system formed by the combination of:
(a) a palladium compound and
(b) at least one organic bidentate phosphine.

25 Claims, No Drawings

PROCESS FOR THE SELECTIVE PREPARATION OF ALKENECARBOXYLIC ACID DERIVATIVES

This is a division of application Ser. No. 127,330 filed Dec. 2, 1987, abandoned.

FIELD OF THE INVENTION

The invention relates to a process for the preparation of alkenecarboxylic acid derivatives by carbonylation of conjugated dienes, in particular to the preparation of 3-pentenoic acid and higher homologues from 1,3-butadiene and higher conjugated dienes. The Invention also includes a novel catalyst containing palladium and multidentate phosphine suitable for said carbonylation process.

BACKGROUND OF THE INVENTION

Processes for the carbonylation of olefinically unsaturated hydrocarbons are known from British Patent Specification No. 1,110,405 and from U.S. Pat. Nos. 4,172,087 and 4,414,409 inter alia.

In the British Patent Specification No. 1,110,405 published Apr. 18, 1968, a process is described for the preparation of esters by the reaction of a diene with carbon monoxide and an alcohol or phenol in the presence of a catalyst containing platinum and/or palladium and/or nickel, and/either
  (a) bromide and/or iodide ions or
  (b)
  (i) a ligand that is able to form a coordination linkage with the metal component of the catalyst and that contains nitrogen, phosphorus, arsenic or sulfur, preference being given to trivalent phosphorus-containing ligands, and particular preference to a primary, secondary or tertiary phosphine or an alkyl, aryl or cycloalkyl phosphite and
  (ii) chloride, bromide or iodide.

Although the conversion of butadiene is mentioned as one of the embodiments, preference is clearly given on page 2, lines 97–103, to dienes as starting compounds, wherein the double bonds are separated by 2, 3 or 4 single bonds. Moreover, the presence of bromide, iodide or chloride is considered to be essential. The reaction is preferred slightly to be performed in an acidified reaction medium by, for example, the presence of toluenesulfonic acid therein.

From the yields of pent-3-enoate obtained in the relevant examples, it will be clear to a person skilled in the art that the aforesaid British patent specification certainly does not provide this expert with any indications for the very selective preparation of pent-3-enoate and higher homologues from 1,3-butadiene and higher conjugated dienes.

From U.S. Pat. No. 4,172,087, issued Oct. 13, 1979, a process is known for the simultaneous preparation of two groups of unsaturated carboxylic acids and esters thereof from aliphatically conjugated diene starting materials containing from 4 to 8 carbon atoms, wherein:
  (a) every two moles of the aliphatically conjugated diene concerned are mixed with a three-component mixture consisting of
    (i) at least a catalytic quantity of a palladium catalyst consisting of either one or more palladium halides in combination with one or more tertiary-phosphorus-containing monodentate donor ligands or one or more halide-free palladium salts in combination with one or more tertiary-phosphorus-containing multidentate donor ligands.
    (ii) at least one molar equivalent of a hydroxyl-group-containing co-reactant selected from the group consisting of water or an aliphatic alcohol containing 1 to 12 carbon atoms, and
    (iii) an (N-heterocyclic) amine base;
  (b) the reaction mixture is pressurized with sufficient carbon monoxide to satisfy the stoichiometry of the carbonylation reaction;
  (c) the pressurized reaction mixture is heated until substantial formation of the desired aliphatic carboxylic acid derivatives has been achieved; and
  (d) the unsaturated carboxylic acid derivatives concerned that occur therein are isolated.

Although the conversion of 1,3-butadiene and aliphatically conjugated diene is mentioned, the presence of an N-heterocyclic base, such as pyridine, alkylated pyridines, quinoline, lutidine, picoline, isoquinoline, alkylated quinolines and isoquinolines, acridine and N-methyl-2-pyrrolidone or N,N-dimethylaniline, N,N-diethylaniline, N,N-diethyltoluidine, N,N-dibutyl-toluidine and N,N-dimethylformamide, is considered to be an essential precondition.

In particular, from the yields of pent-3-enoate mentioned in the described examples, it will be clear to an expert that the process according to the aforesaid U.S. Pat. No. 4,172,087 certainly gives no indications for a very selective preparation of pent-3-enoate and higher homologues from 1,3-butadiene and higher conjugated dienes.

From the U.S. Pat. No. 4,414,409, issued Nov. 8, 1983, a carbonylation process is known for the preparation of acids and esters by conversion of an olefinically unsaturated compound, carbon monoxide and a hydroxyl compound at about 50° C. to about 150° C., in the presence of a catalyst consisting of an organic phosphine ligand palladium complex and a perfluorosulfonic acid.

A clear preference is, moreover, indicated in column 2, lines 26–29, and in column 9, line 27, for the conversion of non-conjugated hydrocarbons.

It will be clear that the processes described hereinbefore are either unsuitable for the conversion of conjugated unsaturated compounds or, in particular, do not seem to be suited to a very selective preparation of 3-pentenoic acid or derivatives and higher homologues, and that those skilled in the art, searching for improved selective preparation methods for 3-pentenoic acid and derivatives thereof, which are becoming an increasingly important starting material for organic syntheses (for example, for the preparation of adipic acid and derivatives thereof), have been diverted away from the methods described hereinbefore.

More in general, a number of known processes have the disadvantage that they use relatively high concentrations of the relevant catalyst system and also use aggressive reaction components, for example, acids such as hydrohalogenic acids or salts thereof and other rigorous reaction conditions, which necessitate cost-increasing measures in connection with safety and the apparatus life (corrosion).

An object of the present invention, therefore, is to provide an improved very selective carbonylation of 1,3-butadiene and higher homologues to very valuable products, such as 3-pentenoic acid or derivatives thereof.

Another object of the present invention is to provide a novel catalytic system for said carbonylation process formed by combining a palladium compound with bidentate phosphine(s).

SUMMARY OF THE INVENTION

An improved process has now been found for the selective conversion of conjugated dienes such as 1,3-butadiene, 1,3-hexadiene and 2,4-heptadiene in liquid phase to the aforesaid compounds with a generally increased conversion rate, in the presence of a characteristic catalyst system and without the presence of (N-heterocyclic) amines and/or halides, whereby cheaper types of steel can be used for the reactor installations.

The invention therefore provides a process for the selective carbonylation of conjugated dienes in the presence of a hydroxyl-group-containing compound such as water, alcohol, phenol or carboxylic acid, in liquid phase and in the presence of a specific catalyst system substantially free of organic nitrogen-containing base that can be formed by combination of (a) a palladium compound and (b) at least one multidentate organic phosphorus ligand.

In particular, the aforesaid process is accomplished in the presence of a catalyst system that can be formed by the combination of (a) a palladium compound and (b) at least one bidentate phosphine derivative with the general formula:

$$R_1R_2 > P-R-P < R_3R_4 \qquad (I)$$

wherein $R_1$, $R_2$, $R_3$ and $R_4$ each represent individually a hydrocarbon group and R represents a divalent organic bridge group with at least 2 carbon atoms in the bridge. In particular, the groups $R_1$ and $R_3$ represent individually an aryl group, preferably phenyl or naphthyl, the groups $R_2$ and $R_4$ represent individually an alkyl group of 1–20 carbon atoms and preferably 2–6 carbon atoms, a cycloalkyl group or an aryl group, and the group R represents an alkylene group of 2–6 carbon atoms, a phenylene or cycloalkylene group.

DETAILED DESCRIPTION OF THE INVENTION

The bidentate phosphine derivative has the following general formula:

$$R_1R_2 > P-R-P < R_3R_4 \qquad (I)$$

wherein $R_1$, $R_2$, $R_3$ and $R_4$ represent individually a hydrocarbon group and R represents a divalent organic bridge group with at least 2 carbon atoms in the bridge. In particular, the groups $R_1$ and $R_3$ represent individually an aryl group, preferably phenyl or naphthyl, the groups $R_2$ and $R_4$ represent individually an alkyl group of 1–20 carbon atoms and preferably 2–6 carbon atoms, a cycloalkyl group or an aryl group, and the group R represents an alkylene group of 2–6 carbon atoms, a phenylene or cycloalkylene group.

As used herein, the term "hydrocarbon group" shall include unsubstituted hydrocarbon group as well as hydrocarbon group bearing one or more substituents selected from the group consisting of alkyl of 1–4 carbon atoms, alkoxy of 1–4 carbon atoms and halogen. Said halogen is preferably fluorine or chlorine.

The terms "aryl group," "alkyl group," "cycloalkyl group," "alkylene group" and "phenyl group" as used hereinafter shall include substituted as well as unsubstituted group(s) and the substituent(s) must be one which would not adversely affect the carbonylation reaction when the bidentate phosphine is used for the catalysis of said reaction.

According to a preferred embodiment, it is possible, depending on the chosen other catalyst components, to add a catalytic quantity of a protonic acid with a pKa value >3 to increase the yield of, for example, pentenoates, in the case of conversion of butadiene at approximately constant high selectivity. The selectivity of, for example, 3-pentenoic acid or derivatives thereof, expressed as a percentage, is defined as:

$$\frac{a}{b} \times 100$$

where "a" is the quantity of 1,3-butadiene converted into 3-pentenoic acid or derivatives thereof, and "b" the total quantity of converted 1,3-butadiene.

It will be clear that the very high selectivity that has been found for the conversion of, for example, 1,3-butadiene into 3-pentenoic acid and derivatives thereof is achieved at the cost of the coincidental formation of 3,8-nonadienic acid or the derivatives thereof, 4-vinyl-1-cyclohexene and 1,3,7-octatriene as in the known earlier process.

Examples of particularly suitable phosphorus ligands are:

1,2-di(diphenylphosphino) ethane,
1,3-di(diphenylphosphino) propane,
1,4-di(diphenylphosphino) butane,
1,5-di(diphenylphosphino) pentane,
1,6-di(diphenylphosphino) hexane,
1,2-tetrafluorocyclobutene diyl bis diphenyl phosphine,
1,2-phenylene bis diphenyl phosphine,
1,2-ethane diyl bis(ditrifluoromethyl) phosphine,
1,3-propane diyl bis(ditrifluoromethyl) phosphine,
1,3-propane diyl bis(trifluoromethyl phenyl) phosphine,
1,2-hexafluorocyclopentene diyl bis diphenyl phosphine,
1,2-tetrafluorocyclobutene diyl bis diphenyl phosphine,
1,2-octafluorocyclohexene diyl bis diphenyl phosphine,
1,4-diphenyl-1,4-diphosphacyclohexane or mixtures thereof.

Very good results are obtained with 1,4-di(diphenylphosphino) butane, 1,3-di(diphenylphosphino) propane and 1,5-di(diphenylphosphino) pentane or mixtures thereof. Moreover, it has been found that good relative conversion results can be obtained if, in addition to the multidentate and preferably bidentate phosphine ligands that are in any case present in the said catalyst system, one or more monodentate phosphine ligands are also present. A particularly preferred group of these last-mentioned compounds includes the group represented by the general formula:

$$\begin{array}{c} R_7 \\ | \\ R_6-P-R_8 \end{array} \qquad (II)$$

wherein $R_6$ represents an aryl group and preferably a phenyl or naphthyl group and $R_7$ and $R_8$ each represent (i) individually an alkyl, cycloalkyl or aryl group; or (ii) $R_7$ and $R_8$ together represent an alkylene or phosphacyclo-alkylene group. Mixtures of these phosphines can also be employed. Preferably, each alkyl group herein contains up to 20 carbon atoms, each cycloalkyl group up to 7 carbon atoms in the ring and each aryl group up to 18 carbon atoms in the ring. An aryl group can represent an anthryl, naphthyl or phenyl group. Phosphines according to Formula II, in which $R_6$ and $R_7$ each represent a phenyl group, form a preferred group. Within this group the phosphines, in which $R_8$ also represents a phenyl group, form a particularly preferred group.

The protonic acids with pKa value >3, which may be added to the catalyst system, preferably consist of benzoic acid or benzoic acids substituted with one or more electron-repelling groups such as 2,4,6-trimethyl benzoic acid, and para-hydroxybenzoic acid.

Both homogeneous and heterogeneous palladium catalyst components can be used for the selective conversion according to the invention. However, homogeneous catalyst systems are preferred. Suitable homogeneous catalyst components are formed by salts of palladium with, for example, nitric acid, sulfuric acid or alkane carboxylic acids containing not more than 12 carbons atoms. Of these, palladium (II) acetate is preferred, however, palladium complexes, such as palladium acetylacetonate, o-toluylphosphine-palladium acetate or bistriphenylphosphinepalladium sulfate can be employed. Palladium linked to an ion exchanger, such as an ion exchanger containing sulfonic acid groups, is an example of a suitable heterogeneous catalyst component. The quantity of palladium is not critical. If a divalent palladium compound is used, preference is given to the use of quantities in the range of between $10^{-5}$ and $10^{-1}$ gram atoms of palladium per mole of conjugated dienes and preferably butadiene.

It has been found that for the best results the molar ratio of the organic phosphorus compound relative to palladium should not be greater than 10 moles phosphine per gram atom of palladium. Very high selectivities and very high conversion rates are achieved if the molar ratio of the phosphine to palladium is between 2 and 5 mole per gram atom of palladium (e.g., 100% conversion of butadiene in 5 hours at 150° C.). It has been found that the proportion of the—possibly added—protonic acid with pKa value >3 should preferably be 6-10 equivalents of acid per gram atom of palladium.

A separate solvent is not essential for the process according to the invention, and often an excess of one of the reactants or products will form a suitable liquid phase. In some cases, however, it may be desirable to use a separate solvent. Any inert solvent can, in principle, be used for this purpose. This can, for example be chosen from sulfoxides and sulfones, for example, dimethyl sulfoxide, diisopropyl sulfone or tetrahydrothiophene 1,1-dioxide (also called sulfolane), 2-methyl-4-butyl sulfolane, 3-methyl sulfolane; aromatic hydrocarbons such as benzene, toluene, xylenes; esters such as methyl acetate and butyrolactone; ketones such as acetone or methyl isobutyl ketone; and ethers such as anisole, 2,5,8-trioxanone (also referred to as diglyme), diphenyl ether and diisopropyl ether or mixtures thereof. Preferably, diphenyl ether is employed.

The process according to the invention enables relatively mild reaction conditions to be used. Temperatures of from 50° C. to 150° C. and more in particular from 20° C. to 100° C. have been found to be very suitable.

The initial pressure of the carbon monoxide can vary over a wide range, but will in general be lower than that of hitherto know processes. Pressures of from 25 to 65 bar are preferred.

In the process according to the invention, the carbon monoxide can be used in its pure form or diluted with an inert gas such as nitrogen, rare gases or carbon dioxide. In general, the presence of more than 5% hydrogen is undesirable, since this can cause hydrogenation of the conjugated diene under the reaction conditions.

The molar ratio of the alcohol, phenol, water or carboxylic acid relative to the conjugated diene, in particular butadiene, can vary between wide limits and generally lies in the range of 0.1:1 to 10:1.

According to a preferred embodiment of the process of the invention, an alcohol can be employed as hydroxyl-containing reactant. The alcohol can be aliphatic, cycloaliphatic or aromatic and can, if necessary, carry one or more inert substituents. A suitable alcohol can contain up to 20 carbon atoms, one or more hydroxyl groups can be present, in which case different products may be formed. For example, a polyvalent alcohol, in particular lower sugars such as glucose, fructose, mannose, galactose, sucrose, aldoxose, aldopentose, altrose, talose, gulose, idose, ribose, arabinose, xylose, lyxose, erythrose or threose, can be reacted with a suitable quantity of butadiene to form a monoester or a polyvalent ester. The choice of the alcohol will therefore only depend on the desired product. Alkanols such as methanol, ethanol, propanol or 2,2-dihydroxymethyl-1-butanol and alcohols containing ether bridges, such as triethylene glycol, all give valuable products.

According to another embodiment of the process of the invention, a great variety of carboxylic acids can be used as reactant. For example, the carboxylic acids can be aliphatic, cycloaliphatic or aromatic and may possible carry inert substituents. Suitable carboxylic acids contain a maximum of 25 carbon atoms. The carboxylic acids used as reactant are preferably alkane carboxylic acids or alkene carboxylic acids. Examples of suitable carboxylic acids are formic acid, acetic acid, propionic acid, n-butyric acid, isobutyric acid, pivalic acid, n-valeric acid, n-caproic acid, caprylic acid, capric acid, lauric acid, myristic acid, palmitic acid, stearic acid, phthalic acid and teraphthalic acid. Examples of alkene carboxylic acids are acrylic acid, propiolic acid, methacrylic acid, crotonic acid, isocrotonic acid, oleic acid, maleic acid, fumaric acid, citraconic acid and mesaconic acid.

The process according to the invention can in principle also be employed with polyvalent carboxylic acids, whereby, depending on the chosen reaction conditions, including the molar ratio of the reactants employed, a variety of products can be obtained as required. If an alkane carboxylic acid is converted according to the process of the invention with 1,3-butadiene, a symmetrical or a composite anhydride can be formed.

Preferably, weak acids are employed for the process according to the invention, with pKa >3 measured in an aqueous medium at 18° C.

Even more preference is given to the employment of acids that cannot be esterified, or only with difficulty, in connection with losses during the process.

The process according to the invention has been found to be particularly suitable for continuous processes, e.g., repeated use of the relevant catalyst system, which offers great advantage for use on an industrial scale.

It will be clear that another aspect of the present invention is formed by the aforesaid catalyst systems, which are used for the selective conversion of conjugated dienes, as such or in the form of a solution in one or more of the suitable, aforesaid solvents.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The invention will now be explained with reference to the following examples, without the invention being thereby limited to these embodiments:

EXAMPLE 1

A 300 ml magnetically stirred HASTELLOY C® autoclave was successively filled with 15 ml ethanol, 40 ml diphenyl ether, 1 mmole palladium acetate and 5 mmole 1,4-di(diphenylphosphino) butane. The autoclave was vacuum-evacuated, whereupon 8 ml of butadiene and carbon monoxide were added to an initial carbon monoxide pressure of 60 bar. The autoclave was heated to 155° C. After a reaction time of 5 hours, the contents of the autoclave were analyzed by means of gas-liquid chromatography. The selectivity of the butadiene to pentenoate conversion was found to be 95%, while the pentenoate yield was 30%, calculated on the starting quantity of butadiene.

EXAMPLE 2

In a virtually analogous manner as described in Example 1, an experiment was performed with a catalyst system composed of palladium acetate (1 mmole) and 1,3-di(diphenylphosphino) propane (1.5 mmole). The selectivity of the butadiene to pentenoate conversion was found to be 92%, while the pentenoate yield, calculated on the starting quantity of butadiene, was 50%.

EXAMPLE 3

In a virtually analogous manner as described in Example 1, an experiment was performed with a catalyst system composed of 1 mmole palladium acetate, 2 mmole 1,4-di(diphenylphosphino) butane and 5 mmole triphenyl phosphine. The selectivity found for the butadiene to pentenoate conversion was 93%, while the pentenoate yield, calculated on the starting quantity of butadiene, was found to be 50%.

EXAMPLE 4

In a virtually analogous manner as described in Example 1, an experiment was performed with the aid of a catalyst system composed of 1 mmole palladium acetate, 4 mmole 1,4-di(diphenyl-phosphino) butane and 7.5 mmole 2,4,6-trimethyl benzoic acid. The reaction temperature was 150° C. and the reaction time was 2.5 hours. The selectivity of the butadiene to pentenoate conversion was found to be 96%, while the pentenoate yield, calculated on the starting quantity of butadiene, was 90%.

EXAMPLE 5

In a virtually analogous manner as described in Example 1, an experiment was performed with the aid of a catalyst system composed of 1 mmole palladium acetate, 2 mmole 1,4-di(diphenylphosphino) butane, 4 mmole triphenyl phosphine and 7.5 mmole 2,4,6-trimethyl benzoic acid. The reaction temperature was 150° C. and the reaction time was 2.5 hours. The selectivity of the butadiene to pentenoate conversion was found to be 91%, while the pentenoate yield, calculated on the starting quantity of butadiene, was found to be 88%.

EXAMPLE 6

In a virtually analogous manner as described in Example 1, an experiment was performed with the aid of a catalyst system composed of 1 mmole palladium acetate, 4 mmole 1,4-di(diphenylphosphino) butane and 7.5 mmole 2,4,6-trimethyl benzoic acid. The initial pressure of the carbon monoxide was 30 bar. The reaction temperature was 150° C. and the reaction time was 2.5 hours. The selectivity of the butadiene to pentenoate conversion was 90%, while the pentenoate yield, calculated on the starting quantity of butadiene, was found to be 89%.

EXAMPLE 7 (FOR COMPARISON)

In a virtually analogous manner as described in Example 1, an experiment was performed with the aid of a catalyst system composed of 1 mmole palladium acetate, 10 mmole triphenyl phosphine and 7.5 mmole 2,4,6-trimethyl benzoic acid. The reaction temperature was 150° C. and the reaction time was 2.5 hours. The selectivity found for the butadiene to pentenoate conversion was 75% (15% of the butadiene was found to have been converted into nonadienoates) and the pentenoate yield, calculated on the starting quantity of butadiene, was 55%.

EXAMPLE 8

In a virtually analogous manner as described in Example 1, an experiment was performed with the aid of a catalyst system composed of 1 mmole palladium acetate and 1.5 mmole 1,2-di(diphenylphosphino) ethane. The selectivity found for the butadiene to pentenoate conversion was 88%, while the pentenoate yield, calculated on the starting quantity of butadiene, was 40%.

EXAMPLE 9

In a virtually analogous manner as described in Example 1, an experiment was performed with the aid of a catalyst system composed of 1 mmole palladium acetate and 4 mmole 1,2,4-di(diphenylphosphino) butane and 7.5 mmole 2,4,6-trimethyl benzoic acid. During the reaction time of 10 hours, additional ethanol and butadiene was added at dosing rates of 25 mmole ethanol/hour and 25 mmole butadiene/hour. The selectivity found for the butadiene to pentenoate conversion was 90%, while the pentenoate yield, calculated on the starting quantity of butadiene was 81%.

What is claimed is:

1. A process for the selective carbonylation of a conjugated diene comprising the steps of contacting said conjugated diene with carbon monoxide in the presence of a hydroxy-group-containing compound selected from the group consisting of water, alcohol, and carboxylic acid, in the liquid phase, using a catalyst system substantially free of organic nitrogen containing base, that can be formed by the combination of
    (a) a palladium compound and
    (b) at least one bidentate organic phosphine derivative with the general formula:

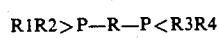

wherein R1, R2, R3 and R4 each represents individually a hydrocarbon or a hydrocarbon bearing one or more substituents selected from the group consisting of alkyl of 1-4 carbon atoms, alkoxy of 1-4 carbon atoms and halogen, and R is individually selected from a group consisting of an alkylene group of 2-6 carbon atoms, a phenylene and a cycloalkylene group.

2. The process as claimed in claim 1, characterized in that the $R_1$ and $R_3$ represent individually an aryl group, $R_2$ and $R_4$ are individually selected from the group consisting of an alkyl group of 1-20 carbon atoms, a cycloalkyl group or an aryl group, and the group R is individually selected from the group consisting of an alkylene group of 2-6 carbon atoms, a phenylene and a cycloalkylene group.

3. The process as claimed in claim 2, wherein said aryl group is phenyl or naphthyl.

4. The process as claimed in claim 1, characterized in that said bidentate phosphine is selected from the group consisting of:
1,2-di(diphenylphosphino) ethane,
1,3-di(diphenylphosphino) propane,
1,4-di(diphenylphosphino) butane,
1,5-di(diphenylphosphino) pentane,
1,6-di(diphenylphospino) hexane,
1,2-tetrafluorocyclobutene diyl bis diphenyl phosphine,
1,2-phenylene bis diphenyl phosphine,
1,2-ethane diyl bis(ditrifluoromethyl) phosphine,
1,3-propane diyl bis(ditrifluoromethyl) phosphine,
1,3-propane diyl bis(trifluoromethyl phenyl) phosphine,
1,2-hexafluorocyclopentene diyl bis diphenyl phosphine,
1,2-tetrafluorocyclobutene diyl bis diphenyl phosphine,
1,2-octafluorocyclohexene diyl bis diphenyl phosphine,
1,4-diphenyl-1,4-diphosphacyclohexane and mixtures thereof.

5. The process as claimed in claim 1, characterized in that said phosphine is selected from the group consisting of 1,4-di(diphenylphosphino) butane, 1,3-di(diphenylphosphino) propane and 1,5-di(diphenylphosphino) pentane and mixtures thereof.

6. The process as claimed in claim 1, characterized in that said palladium compound is palladium (II) acetate.

7. The process as claimed in claim 1, characterized in that a quantity of $10^{-5}$ to $10^{-1}$ gram atoms palladium per mole conjugated diene is employed.

8. The process as claimed in claim 1, characterized in that the molar ratio of the phosphine ligand to palladium is between about 2 and about 5 moles per gram atom palladium.

9. The process as claimed in claim 1, characterized in that an additional solvent is used.

10. The process as claimed in claim 9, characterized in that the solvent is selected from the group consisting of sulfoxides, sulfones, aromatic hydrocarbons, esters, ketones, ethers and mixtures thereof.

11. The process as claimed in claim 10, wherein said solvent is selected from the group consisting of dimethyl sulfoxide, diisopropyl sulfone, tetrahydrothiophene 1,1-dioxide (sulfolane), 2-methyl-4-butyl sulfolane, 3-methyl sulfolane, benzene, toluene, xylene, methyl acetate, butyrolactone, acetone, methyl isobutyl ketone, anisole, 2,5,8-trioxanone (diglyme), diphenyl ether and diisopropyl ether.

12. The process as claimed in claim 10, characterized in that said solvent is diphenyl ether.

13. The process as claimed in claim 1, characterized in that the molar quantity of said hydroxyl-group-containing compound per mole of diene is between about 0.1:1 and about 10:1.

14. The process as claimed in claim 1, characterized in that said conjugated diene is 1,3-butadiene.

15. A process for the selective carbonylation of a conjugated diene comprising the steps of contacting said conjugated diene with carbon monoxide in the presence of a hydroxy-group-containing compound selected from the group consisting of water, alcohol, and carboxylic acid, in the liquid phase, using a catalyst system substantially free of organic nitrogen containing base, that can be formed by the combination of
(a) a palladium compound,
(b) at least one bidentate organic phosphine derivative with the general formula:

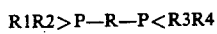

wherein R1, R2, R3 and R4 each represents individually a hydrocarbon or a hydrocarbon bearing one or more substituents selected from the group consisting of alkyl of 1-4 carbon atoms, alkoxy of 1-4 carbon atoms and halogen, and R is individually selected from a group consisting of an alkylene group of 2-6 carbon atoms, a phenylene and a cycloalkylene group, and
(c) a catalytic quantity of a protonic acid with a pKa value $>3$.

16. The process as claimed in claim 15, characterized in that the protonic acid is a benzoic acid.

17. The process as claimed in claim 15, wherein said protonic acid is selected from the group consisting of 2,4,6-trimethyl benzoic acid and para-hydroxy benzoic acid.

18. The process as claimed in claim 15, characterized in that 6-10 equivalents of a protonic acid with a pKa value $>3$ per gram atom palladium is used.

19. A process for the selective carbonylation of a conjugated diene comprising the steps of contacting said conjugated diene with carbon monoxide in the presence of a hydroxy-group-containing compound selected from the group consisting of water, alcohol, and carboxylic acid, in the liquid phase, using a catalyst system substantially free of organic nitrogen containing base, that can be formed by the combination of
(a) a palladium compound;
(b) at least one bidentate organic phosphine derivative with the general formula:

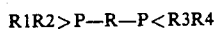

wherein R1, R2, R3 and R4 each represents individually a hydrocarbon or a hydrocarbon bearing one or more substituents selected from the group consisting of alkyl of 1-4 carbon atoms, alkoxy of 1-4 carbon atoms and halogen, and R is individually selected from a group consisting of an alkylene group of 2-6 carbon atoms, a phenylene and a cycloalkylene group; and
(c) at least one monodentate phosphine ligand with the following formula:

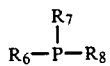

wherein R₆ represents an aryl group and R₇ and R₈ are (i) individually selected from the group consisting of alkyl, a cycloalkyl and an aryl group, or (ii) R₇ and R₈ together represent an alkylene or a phosphacyclo-alkylene group.

20. The process as claimed in claim 19, characterized in that the monodentate phosphorus ligand is a phosphine or a mixture of phosphines with the following formula:

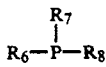

wherein R₆ represents an aryl group and R₇ and R₈ are (i) individually selected from the group consisting of alkyl, a cycloalkyl and an aryl group, or (ii) R₇ and R₈ together represent an alkylene or a phosphacyclo-alkylene group.

21. The process as claimed in claim 19, characterized in that R₆, R₇ and R₈ are individually a phenyl group.

22. A process for the selective carbonylation of butadiene comprising the steps of contacting said butadiene with carbon monoxide in the presence of ethanol using a catalyst formed by the combination of palladium acetate, a phosphine which is 1,4-di(diphenylphosphino) butane or 1,3-di(diphenyl phosphino) propane, and a monodentate phosphine or a mixture of monodentate phosphines with the following formula:

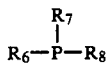

wherein R₆ represents an aryl group and R₇ and R₈ are (i) individually selected from the group consisting of alkyl, a cycloalkyl and an aryl group, or (ii) R₇ and R₈ together represent an alkylene or a phosphacyclo-alkylene group.

23. The process as described in claim 22, wherein said monodentate phosphine is triphenyl phosphine.

24. A process for the selective carbonylation of butadiene comprising the steps of contacting said butadiene with carbon monoxide in the presence of ethanol using a catalyst formed by the combination of palladium acetate, a phosphine which is 1,4-di(diphenylphosphino) butane or 1,3-di(diphenyl phosphino) propane, and a catalytic quantity of an acid selected from the group consisting of 2,4,6-trimethyl benzoic acid, para-hydroxy benzoic acid, meta-hydroxy benzoic acid and mixtures thereof.

25. A process for the selective carbonylation of butadiene comprising the steps of contacting said butadiene with carbon monoxide in the presence of ethanol using a catalyst formed by the combination of palladium acetate and a phosphine which is 1,4-di(diphenyl phosphino) butane or 1,3-di(diphenyl phosphino) propane.

* * * * *